(12) United States Patent
Shindo et al.

(10) Patent No.: US 7,955,077 B2
(45) Date of Patent: Jun. 7, 2011

(54) OCCLUSION CORRECTION INSTRUMENT AND METHOD OF USE

(76) Inventors: Mitsuo Shindo, Yamanashi (JP); Mihoko Shindo, Yamanashi (JP)

( * ) Notice: Subject to any disclaimer, the term of this patent is extended or adjusted under 35 U.S.C. 154(b) by 0 days.

(21) Appl. No.: 12/379,101

(22) Filed: Feb. 12, 2009

(65) Prior Publication Data

US 2009/0155738 A1   Jun. 18, 2009

Related U.S. Application Data

(63) Continuation of application No. 11/282,468, filed on Nov. 21, 2005, now abandoned.

(30) Foreign Application Priority Data

Feb. 1, 2005 (JP) ................. 2005-025459
Aug. 30, 2005 (JP) ................. 2005-248903

(51) Int. Cl.
*A61C 19/04* (2006.01)
(52) U.S. Cl. ............. 433/68; 433/72; 433/73; 33/514
(58) Field of Classification Search .............. 433/68, 433/69, 72, 73, 75; 33/513, 514
See application file for complete search history.

(56) References Cited

U.S. PATENT DOCUMENTS

| 1,776,474 | A | 9/1930 | Messerman |
| 2,255,267 | A | 9/1941 | Moran |
| 2,301,358 | A | 11/1942 | Ballard |
| 2,389,063 | A | 11/1945 | Lang |
| 2,481,203 | A | 9/1949 | Davies et al. |
| 2,562,106 | A | 7/1951 | Leathers |
| 2,612,688 | A | 10/1952 | Avary |
| 2,994,957 | A | 8/1961 | McLeod |
| 3,564,717 | A | 2/1971 | Ennor |

(Continued)

FOREIGN PATENT DOCUMENTS

DE   3528621   3/1989

(Continued)

OTHER PUBLICATIONS

Japanese Office Action issued Jul. 15, 2008 (with English translation) in connection with Japanese Patent Application No. 2005-248903, which is a foreign counter part of the present application.

*Primary Examiner* — John J Wilson
(74) *Attorney, Agent, or Firm* — Wenderoth, Lind & Ponack, L.L.P.

(57) ABSTRACT

An occlusion correction improvement instrument includes an upper mold-mounting member provided with a plate-shaped member that is parallel to a Camper's plane of an upper model having a tooth model-shaped surface of a maxillary tooth row and with a plane parallel to the Camper's plane when the upper mold-mounting member has been mounted on the upper model; and a lower mold-mounting member mountable on a lower model having a tooth model-shaped surface of a mandible tooth row and provided with a pin-shaped projection portion that can be fixed, with a position thereof adjusted from side to side and up and down, and with an adjustment member that can adjust a position of the lower mold-mounting member relative to the upper mold-mounting member on the plane parallel to the Camper's plane, with the projection portion abut on the plate-shaped member of the upper mold-mounting member.

10 Claims, 10 Drawing Sheets

U.S. PATENT DOCUMENTS

| | | |
|---|---|---|
| 4,306,861 A | 12/1981 | Dickson |
| 5,163,841 A | 11/1992 | Schreinemakers |
| 5,188,529 A | 2/1993 | Luth |
| 6,106,285 A | 8/2000 | Kwak |
| 6,152,730 A | 11/2000 | Wildman |
| 2002/0032449 A1 | 3/2002 | Rota et al. |
| 2005/0277086 A1* | 12/2005 | Arai et al. .................... 433/54 |

FOREIGN PATENT DOCUMENTS

| | | |
|---|---|---|
| JP | 5-192358 | 8/1993 |
| JP | 2001-276098 | 10/2001 |
| JP | 2003-220079 | 8/2003 |
| JP | 2004-73628 | 3/2004 |
| WO | 8700747 | 2/1987 |

* cited by examiner

OCCLUSION CORRECTION INSTRUMENT AND METHOD OF USE

This application is a continuation of U.S. application Ser. No. 11/282,468 filed Nov. 21, 2005 now abandoned.

BACKGROUND OF THE INVENTION

1. Field of the Invention

The present invention relates to an occlusion correction improvement instrument for making the occlusal treatment so that the maxilla and the mandible may make correct occlusion in the physiologic positional relationship between the cranial bone and the mandible bone and to an occlusion correction improvement method using the instrument.

2. Description of the Prior Art

In the constitution of the occlusion section in a human body, the mandible bone and the mandible tooth row are suspended by means of muscles from the brainpan while the maxillary bone and the maxillary tooth row are attached to the brainpan. For this, even when the mandible section intrinsically has a correct relationship in occlusion relative to the maxillary section, there is a possibility of the mandible section deviating spontaneously from the maxillary section due to the common practice and bad habits of the chewing cycle during the mastication over a long period of time, the action of gravitational pull of the earth, etc. Within the mouth, there is an operation side (right or left) on which food is chewed more strongly and a non-operation side (left or right) opposed to the operation side. The difference in the chewing motion on the opposite sides during the chewing movement produces a time lag in the occlusion section, thereby possibly deviating the mandible to the rightward, leftward or backward direction.

When the mandible has deviated from the cranial bone, the central line of the face called "the median line" deviates to change the facial configuration. Furthermore, the deviation of the mandible making the role of a balancer relative to the gravitational pull of the earth produces a distortion from the face to the whole-body posture or a change of the walking manner to possibly exert a burden onto the internal organs and possibly induce symptoms called "the indefinite complaints" that are physical complaints, such as general malaise, dizziness, headache, palpitation, diarrhea, etc. Therefore, the occlusal treatment has heretofore been made. The occlusal treatment is aimed at correcting occlusion between the maxilla tooth row and the mandible tooth row to stabilize the positional relationship of the mandible relative to the cranial bone and at forming an intercuspation section that enables the chewing cycle during the mastication by the maxilla tooth row and mandible tooth row to be maintained in a stable state.

As means for correcting the positional relationship between the cranial bone and the mandible bone, a mandible position correction instrument for correcting the position of the mandible relative to the maxilla has been proposed (JP-A 2004-73628). The mandible position correction instrument comprises a floor extending along a superior dental arch, a maxilla teeth engagement portion formed on the inside surface of the floor, a mandible function cuspis dentis flat vestige formed on the occlusion surface of the floor, a pair of left and right ball clasps provided on the floor correspondingly between the first and second bicuspid teeth of the maxilla and a pair of simple hooks provided on the floor correspondingly respectively to the left and right second molar teeth of the maxilla. By mounting this mandible correction instrument on the maxilla to guide the mandible to a predetermined position relative to the maxilla during the course of occlusion between the maxilla teeth and the mandible teeth, thereby depriving a patient of the indefinite complaints.

As another means for correcting the occlusion, an occlusion adjustment gauge plate provided with a median line (the general gravity line) provided at the center of a transparent flat plate, lines showing the positions of the buccal cuspis dentis apexes on the cheek side of the opposite first bicuspid teeth in parallel to the median line and in a symmetry fashion, a line showing the contact point between the canine tooth and the first bicuspid tooth and orthogonal to these lines, and a line connecting the centrifugal adjacent contact points of the opposite first molar teeth has been proposed (JP-A 2001-276098). This occlusion adjustment gauge plate is designed to detect the distortion and accurate position of the dental arch during the course of the occlusion by using a transparent flat plate as a substrate and adjusting all the teeth of the maxilla and mandible to be in contact with the surface of the gauge.

Under the present circumstances, however, physicians that make the dental treatment (dentists) rely greatly on their own experiences and gut feelings encountered so far in performing the occlusion treatment. Furthermore, since occlusion treatments by various operative methods exist, it is under the present circumstances that the dentists have actually adopted different operative methods they believe to be the best as the occlusion treatment. Therefore, this has raised the problems that the results of improvement on the symptoms obtained by the occlusion treatment differs from one another and that the time required for the occlusion treatment is not constant. Particularly, it has raised a serious problem to the patients that the technical levels of the dentists are not constant. Furthermore, since patients have different symptoms, respectively, when they have undergone the same occlusion treatment by the same dentist, the same treatment effect could not be obtained.

For example, the chewing cycle is classified into a so-called grinding type that is an occlusion type of motion such as grinding food by the lateral movement of the jaws during the teeth occlusion and a so-called chopping type that is an occlusion type of moving the jaws in the longitudinal direction, with the lateral movement of the jaws prevented by some abnormality or other. In the case of performing the occlusion treatment for the purpose of attaining the physical restoration of the occlusion, when all the physical restoration is to be exclusively applied to the chopping type, persons performing the occlusion of the grinding type will encounter an additional occlusion dysfunction. Since the chewing functional movement is an integrated series of motions of the jaw joints, nerves, muscles, tooth rows and occlusion faces, these are to be all taken into consideration when performing the occlusal treatment. The mandible position correction instrument of JP-A 2004-73628 is mounted onto the maxillary teeth to be contemplating positional correction of the mandible by occlusion of the maxillary teeth and mandible teeth. Since a superior dental arch on which the instrument is mounted, a desired position of the mandible teeth, etc. are not explicitly described in the prior art, no technical source that enables the mounted instrument to correct the positional relationship between the maxillary teeth and the mandible teeth to a correct one is disclosed. Furthermore, since no method for manufacturing the instrument is disclosed, the instrument is difficult to manufacture.

The occlusion adjustment gauge plate of JP-A 2001-276098 is manufactured based on the data of an average dental arch for Japanese persons belonging to the mongoroid human beings. Since the differences among individuals on the upper and lower tooth rows are not taken into consideration, it is difficult to say that this gauge plate is an instrument that can realize ideal occlusion for individual patients, and there is a fair possibility of an individual difference in the occlusion treatment effect arising among the patients. Furthermore, the gauge plate when a patient has performed occlusion between the upper and lower tooth rows is difficult to visually discern from the outside, resulting in difficulty to make correct measurements. Moreover, since this gauge plate is an instrument having gauges inscribed on a plate at prescribed intervals, it cannot reply to the differences in width and length of the patients' tooth rows. This means the preparation of a great number of various kinds of gauge plates is required so as to deal with tooth rows of different sizes, resulting in occurrence of cumbersome measurement in compliance with patients and time-consuming work. What is worse, where there is no gauge plate suitable for a patient, correct measurements cannot be made. Further, there is also another related technology (for example, WO 87/00747) in which attention is focused on a Camper's plane and an upper mold-mounting member provided with a plane that is parallel to the Camper's plane is used, thereby realizing appropriate occlusion correction.

However, in all the above-mentioned conventional technologies, the occlusion correction is performed based on a positional relationship between the Camper's plane, the upper mold-mounting member, and the like only in the head (living body) of the patient. The inventors of the present invention have found that the occlusion correction performed based thereon does not lead to a fundamental improvement. That is, the patient's head is a parenchyma which differs among individuals. For example, positions of right and left ears and depths thereof are different with each other. Accordingly, by using those as reference, there is performed the occlusion correction with torsion. As a result, in a state where a human being is standing, even if the person feels that he or she is standing upright, in fact, the person is inclined to some degree. Accordingly, the inventors of the present invention are the first one who have noted that, the Camper's plane has to be set by making a consideration to difference in inclination among individual patients, otherwise it is impossible o provide an appropriate occlusion correction improvement instrument for each patient. The present invention has been developed as a result of the keen studies in view of the present state of affairs and the object thereof is to provide an occlusion correction improvement instrument capable of providing the occlusal treatment of the positions of the cranial bone and mandible that manifests an extremely high level of therapeutic effect for each patient based on a relationship between a gravitational pull and a center of gravity of the individual patient's head, restoring the facial configuration to deprive a patient of the indefinite complaint and correcting a patient's whole-body posture distortion. Thus, the instrument of the present invention can provide body correction treatment relative to all diseases thought to result from inappropriate occlusion-related treatment, thereby contributing to the health of the entire body. That is, the inventors of the present invention have fond that, regarding a balance of the occlusion of the maxilla and the manible, an optimum occlusion position can be determined based on the gravitational pull and the center of gravity, and the above-mentioned object can be achieved by determining the occlusion position at the center of gravity.

SUMMARY OF THE INVENTION

To attain the above object, the present invention provides, as a first aspect thereof, an occlusion correction improvement instrument comprising an upper mold-mounting member provided with a plate-shaped member that is parallel to a Camper's plane of an upper model having a tooth model-shaped surface of a maxillary tooth row and with a plane parallel to the Camper's plane when the upper mold-mounting member has been mounted on the upper model. The occlusion correction improvement instrument also comprises a lower mold-mounting member mountable on a lower model having a tooth model-shaped surface of a mandible tooth row and provided with a pin-shaped projection portion that can be fixed, with a position thereof adjusted from side to side and up and down, and with an adjustment member that can adjust a position of the lower mold-mounting member relative to the upper mold-mounting member on the plane parallel to the Camper's plane, with the projection portion abut on the plate-shaped member of the upper mold-mounting member.

In a second aspect of the invention that includes the first aspect thereof, the plate-shaped member is mounted on the upper mold-mounting member using a jig for acquiring a plane parallel to the Camper's plane of the upper model.

In a third aspect of the invention that includes the first or second aspect thereof, the lower mold-mounting member has a plate member having a frame body, and the projection portion has a proximal part helically engaged with the plate member so as to be movable vertically relative to the plate member and horizontally relative to the frame body.

In a fourth aspect of the invention that includes any one of the first to third aspects thereof, the projection has a distal end formed into a semi-spherical shape in cross section.

The present invention also provides an occlusion correction improvement method comprising a step of acquiring a plane parallel to a Camper's plane of an upper model having a tooth model-shaped surface of a maxillary tooth row, and a step of forming an upper mold-mounting member that comprises an upper frame mountable on the upper model and a plate-shaped member attached to the upper frame in parallel to the parallel plane. The occlusion correction improvement method also comprises a step of forming a lower mold-mounting member that comprises a lower frame mountable on a lower model having a tooth model-shaped surface of a mandible tooth row and an adjustment member attached to the lower model and provided with a pin-shaped projection portion that is movable side to side and up and down relative to the lower frame and capable of abutting on the plate-shaped member of the upper mold-mounting member. The occlusion correction improvement method further comprises a step of correction including adjustment of a position of the projection portion, adjustment of a position of the lower mold-mounting member relative to the upper mold-mounting member in the presence of a change of the relative position from a state wherein the projection portion is abut on the plate-shaped member in a neighborhood of a center portion thereof and a pretreatment of excavation or prosthesis.

In a sixth aspect of the invention that includes the fifth aspect thereof, the plate-shaped member is mounted on the upper mold-mounting member using a jig for acquiring a plane parallel to the Camper's plane of the upper model at the step of forming the upper mold-mounting member.

In a seventh aspect of the invention that includes the fifth or sixth aspect thereof, the lower mold-mounting member is provided with a plate member having a frame body, and the projection portion has a proximal part helically engaged with the plate member so as to be movable vertically relative to the plate member and horizontally relative to the frame body at the step of forming the lower mold-mounting member.

In an eighth aspect of the invention that includes any one of the fifth to seventh aspects thereof, the projection has a distal end formed into a semi-spherical shape in cross section at the step of forming the lower mold-mounting member.

According to the first aspect of the invention, an occlusion correction improvement instrument is provided with which occlusal treatment manifesting an extremely high effect can be made irrespective of dentists' experiences or levels of technique, and occlusion of the cranial bone and mandible can be cured appropriately in conformity to the symptom of a patient to correct the distortion in the patient's facial configuration, eliminate the indefinite complaint and correct the distortion of the patient's entire body posture, thereby contributing to an improvement in the health condition of the patient's body. In addition, the patient having undergone the occlusal treatment enjoys good occlusion and can make correct chewing movement and bite food and even hard food off with his or her teeth into minute pieces. This is running on prevention of not only dental diseases, such as caries, alveolar pyorrhea, etc. but also other diseases by body correction treatment. Also, this treatment can be made by simple and explicit procedures.

According to the second aspect of the invention, an occlusion correction improvement instrument is provided which is capable of exactly acquiring a different Camper's plane for every one patient, accurately measuring the patient's occlusion state and making correct treatment.

According to the third aspect of the invention, an occlusion correction improvement instrument is provided which is capable of being used even in the case where the position of the mandible is deviated relative to the brainpan through the inappropriate occlusion over a long period and visually discerning the position of the mandible relative to the brainpan.

According to the fourth aspect of the invention, an occlusion correction improvement instrument is provided which is capable of reducing the friction of the distal end of the projection portion against the plate-shaped member, allowing the projection portion to move smooth onto the plate-shaped member and describe its track on the surface of the plate-shaped member, thus showing the state of occlusion of the maxillary and mandible tooth rows with exactitude, and capable of visually discerning the state with ease from outside.

According to the fifth aspect of the invention, an occlusion correction improvement method is provided by which occlusal treatment manifesting an extremely high effect can be made through prescribed standardized steps and irrespective of dentists' experiences or levels of technique, and occlusion of the cranial bone and mandible can be cured appropriately in conformity to the symptom of a patient to correct the distortion in the patient's facial configuration, eliminate the indefinite complaint and correct the distortion of the patient's entire body posture, thereby contributing to an improvement in the health condition of the patient's body. In addition, the patient having undergone the occlusal treatment enjoys good occlusion and can make correct chewing movement and bite food and even hard food off with his or her teeth into minute pieces. This is running on prevention of not only dental diseases, such as caries, alveolar pyorrhea, etc. but also other diseases by body correction treatment.

According to the sixth aspect of the invention, an occlusion correction improvement method is provided which is capable of exactly acquiring a different Camper's plane for every one patient, accurately measuring the patient's occlusion state and making correct treatment.

According to the seventh aspect of the invention, an occlusion correction improvement method is provided that can provide a lower mold-mounting member capable of replying even to the case where the position of the mandible is deviated relative to the brainpan through the inappropriate occlusion over a long.

According to the eighth aspect of the invention, an occlusion correction improvement method is provided that can provide a lower mold-mounting member capable of reducing the friction of the distal end of the projection portion against the plate-shaped member, allowing the projection portion to describe its track on the surface of the plate-shaped member with exactitude, thus showing the state of occlusion of the maxillary and mandible tooth rows with exactitude, and capable of visually discerning the state with ease from outside The above and other objects, characteristic features and advantages of the present invention will become apparent to those skilled in the art from the description to be made herein below with reference to the accompanying drawings.

DETAILED DESCRIPTION OF THE PREFERRED EMBODIMENTS

One embodiment of each of the occlusion correction improvement instrument and the occlusion correction improvement method according to the present invention will be described in detail with reference to the accompanying drawings.

A physician that makes dental treatments (dentist) first asks a patient about his or her condition and examines the patient. This includes checking the symptoms of the muscle in the state of occlusion of the maxilla and mandible before a dental treatment, taking photographs of the inside of the oral cavity and the entire body, taking an X-ray fluoroscopic picture, etc. to acquire a denture mold and thereafter a model 10 of this denture mold is produced. The denture mold model 10 is produced in accordance with an ordinary production method that comprises, for example, forming molds of the maxillary tooth row and mandible tooth row M and N and pouring gypsum into the molds. The model 10 comprises an upper model 11 having the maxillary tooth row M and a lower model 12 having the mandible tooth row N.

Figure 3:
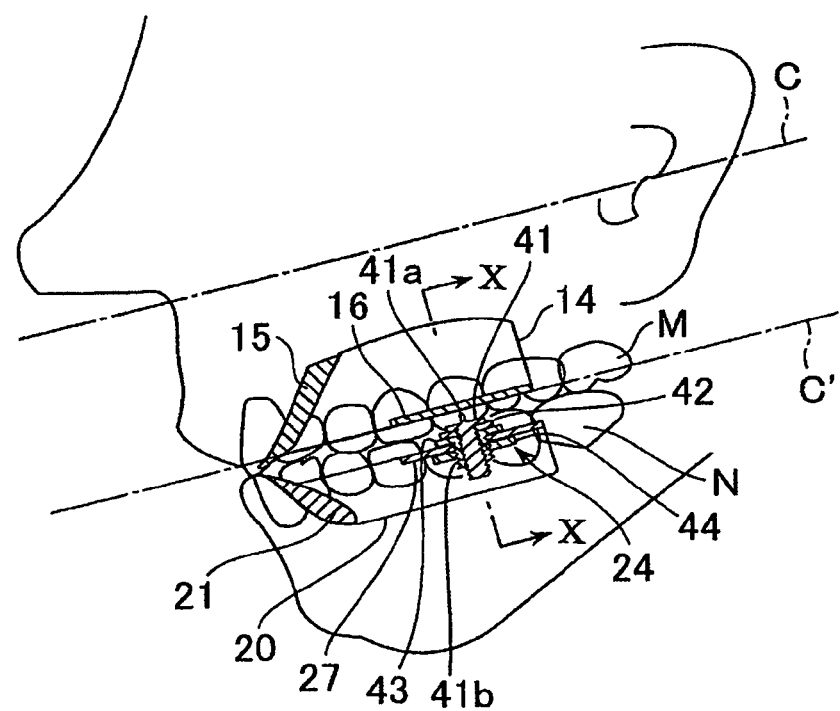
FIG. 3 is an explanatory view illustrating a mounted state of the occlusion correction improvement instrument.

In FIG. 3, a plane C' in parallel to a Camper's plane C of the patient is determined within the oral cavity of the patient. The Camper's plane C is a virtual plane when setting an occlusion plane. Though it is defined as a virtual plane connecting a horizontal coordinate P of the lower point of the ala nasi in FIG. 9 and a horizontal coordinate Q of the upper edge of the auditory meatus, there is an actual case where a virtual plane connects the lower point of the ala nasi and the horizontal plane of the lower edge of the auditory meatus. Therefore, a preferable Camper's plane may be selected in accordance with the facial configuration, the occlusion state of the maxillary tooth row and mandible tooth row M and N etc. of the patient. The Camper's plane is obtained using a prescribed device mounted on a human body. While in the present embodiment a headgear like device is used, different modes of devices, such as an eyeglass like device, may be adopted.

Figure 13:
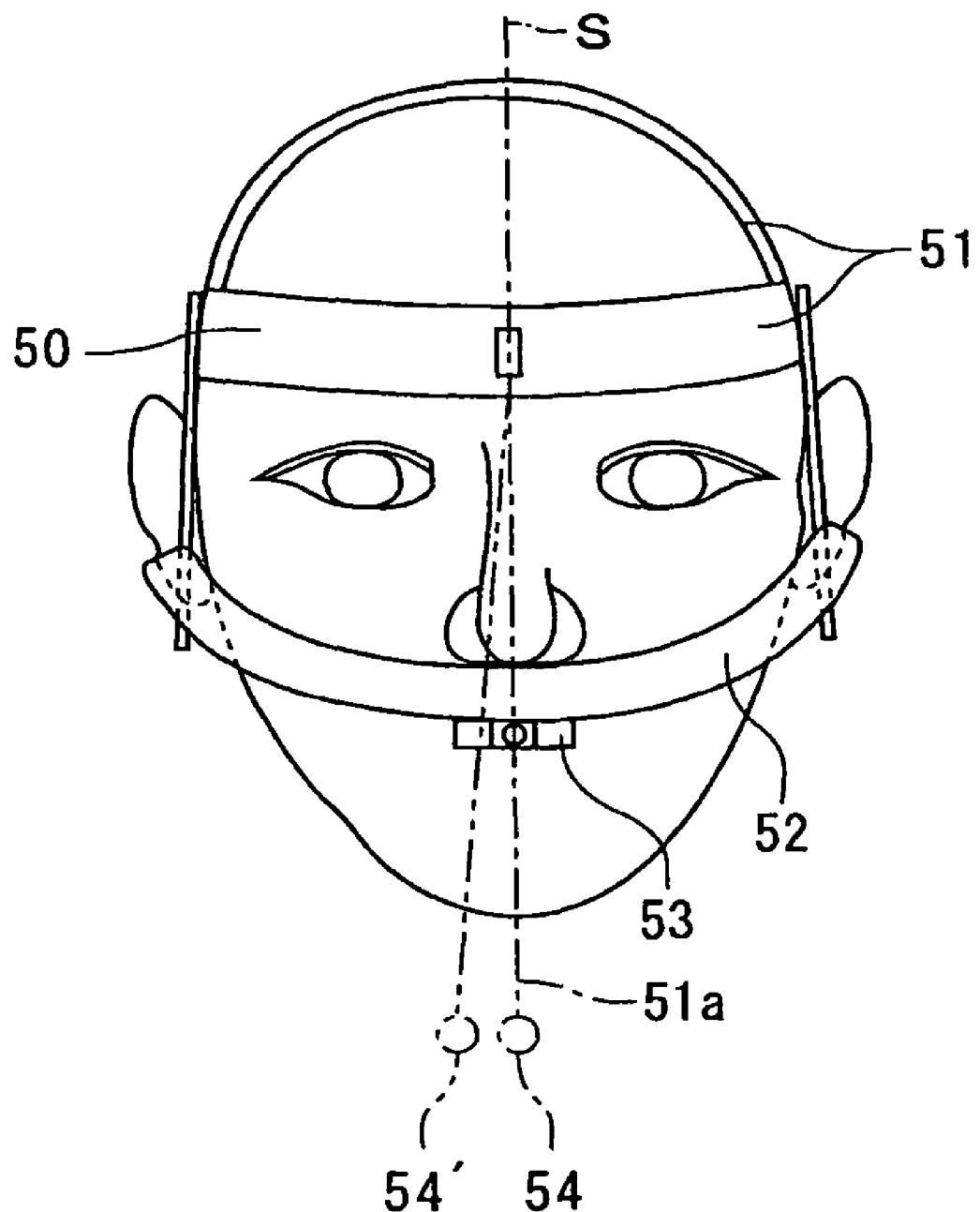
FIG. 13 is a front view showing the state of a plane-acquiring device mounted onto the head.
Figure 14:
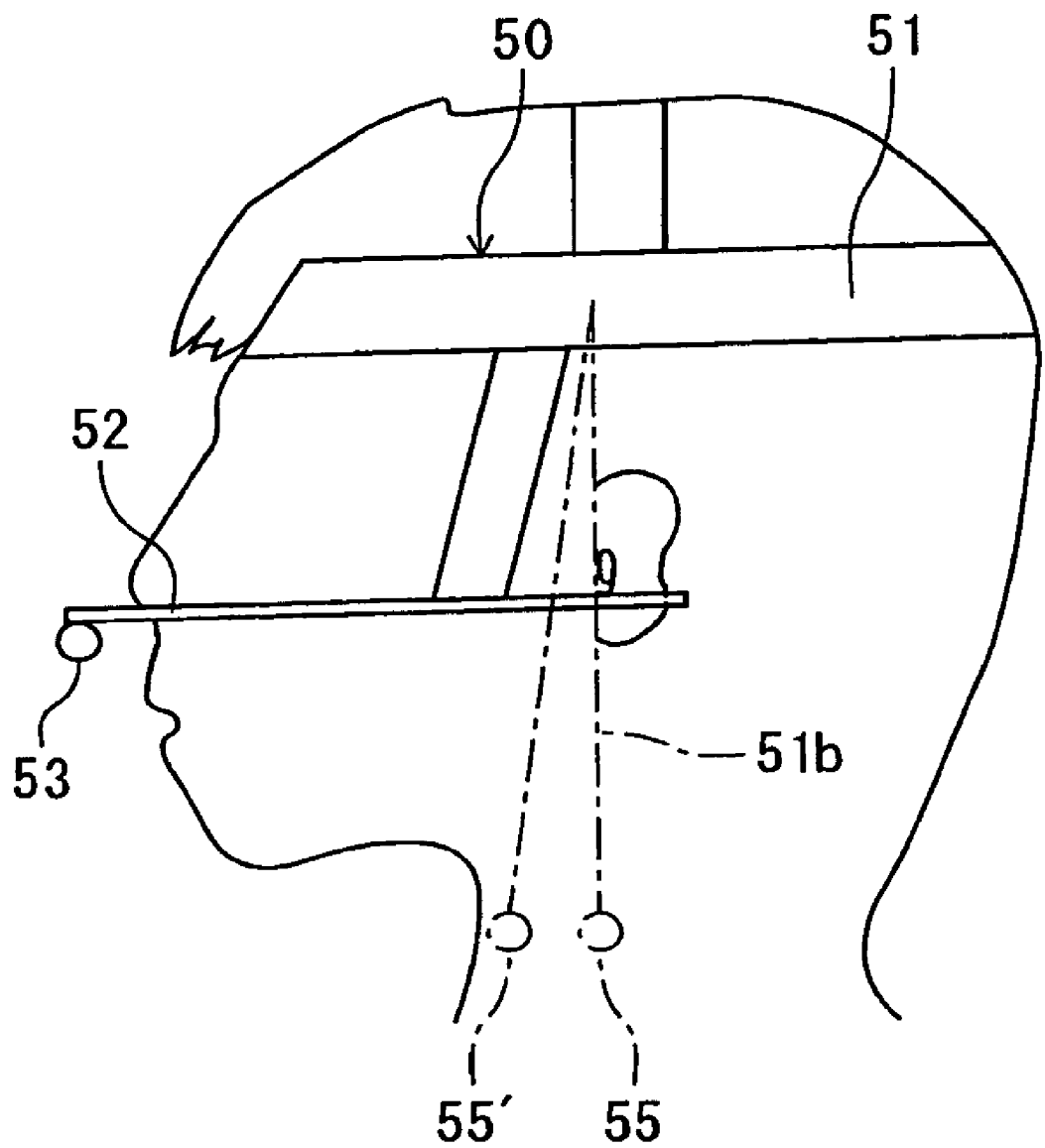
FIG. 14 is a side view showing the state of the plane-acquiring device mounted onto the head.

FIG. 13 and FIG. 14 show one example of a headgear like Camper's plane-acquiring device 50. The plane-acquiring device 50 comprises a strap member 51 mounted on the head, a plane member 52 in the shape of a boomerang attached as being suspended from the strap member 51 and laying in the direction moving across the face, and a plane-measuring member 53 that is a level provided substantially at the center of the plane member 52. For example, the neighborhood of the center of the plane member 52 is provided with markings at intervals of around 5 mm. In this case, the amount of deviation from the center portion (the center of gravity) can be numerically recorded. The plane-measuring member 53 may also be attached to each of the right and left sides of the plane member 52. The strap member 51 is provided at the center thereof on the face side with a string-member 51a having a weight 54 suspended from the distal end thereof. As shown in FIG. 14, a weight 55 is suspended from the distal end of each of the string-members 51b provided on the right and left sides of the strap member 51.

When the plane-acquiring device 50 is mounted on the head, the strap member 51 is used to surround the head and is fixed to the head with press-on and split-off (Velcro) fasteners (not shown) provided on the strap member 51. By the use of the Velcro fasteners, the strap member can be fit to the head irrespective of the size of the head of a patient.

Figure 9:
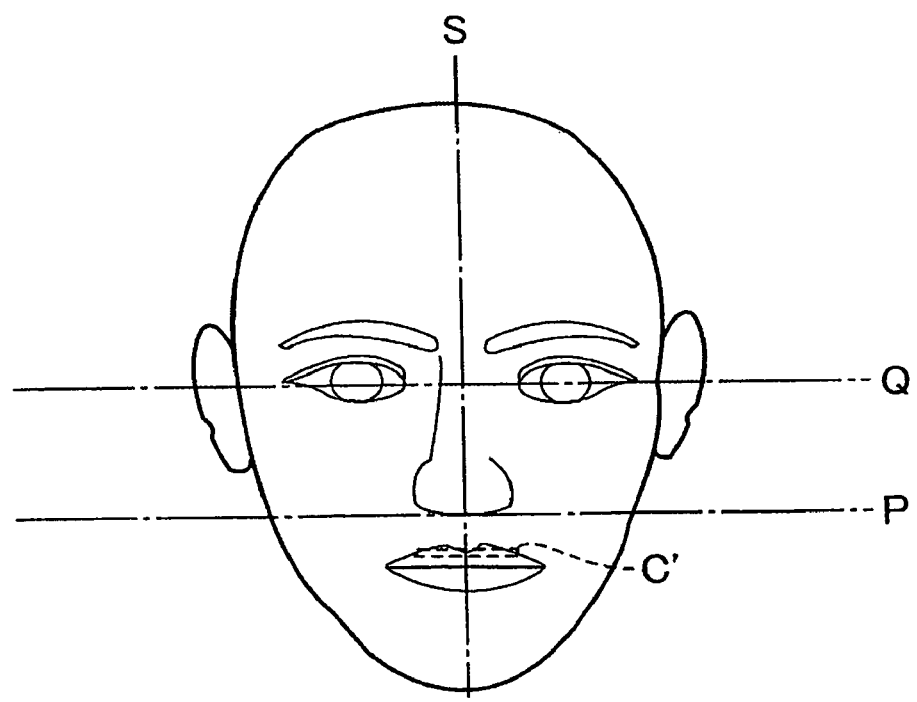
FIG. 9 is a front view showing the state of occlusion of the maxilla and mandible.

Next, the plane member 52 is mounted while being adjusted to be along the virtual plane connecting the horizontal coordinate P of the lower point of the ala nasi in FIG. 9 and the horizontal coordinate Q of the edge of the auditory meatus (opening of external acoustic meatus), In this case, adjustment is performed by viewing the level mounted to the plane member 52 so that the plane member 52 levels in a normal horizontal direction. As a result, a plane in parallel to the Camper's plane can be obtained with the plane member 52. Where the right and left openings of the external acoustic meatus differ in height position when the plane member 52 is mounted, the height positions are to be set to the average height of the right and left ears while visually discerning the inclination state shown on the plane-measuring member 53. When the head of the patient is deprived of the fixation from this state, the head is inclined because the patient is achieving a balance of the head from the habitual occlusion state. By this head inclination, the patient is achieving a physical balance.

The dentist measures an inclination of the center of gravity of the patient's head, i.e. the cranial bone inclination called rolling, and the cranial bone anteroposterior inclination, i.e. cranial bone inclination called pitching, from the degrees of inclination of the string-members 51a and 51b, respectively. The height of the eyes, position of the oral angle, heights of the shoulders, etc. are also confirmed. Particularly, the angle of a line connecting the torus occipitalis and the lower line of the arcus zygomaticus is observed. As regards the inclination of the center of gravity of the head, for example, the state of the weight 54' in FIG. 13 indicates the state of the head inclined on the observer's left, and the state of the weight 55' in FIG. 14 indicates the state of the head inclined forward.

The dentist executes an occlusion correction treatment which will be described later based on the inclinations of the string-members 51, 51a and 51b by the weights 54 and 55 to bring the mandible bone to a stable position of the center of gravity. In proportion as the center of gravity of the head is brought to a correct state, the angles of inclination of the string-members 51a and 51b are made small and the angle of the head is made also small. The amount of forward movement of the head can also be confirmed from the positional relationship between the sagittal line passing through the opening of external acoustic meatus and the acromioclavicular joint. When the rolling and pitching are brought to the respective correct states after the occlusion treatment, the inclinations of the string-members become close to the median line S. By continuing the occlusion treatment until the weights come to their respective correct positions from their inclinations, the center of gravity of the head is corrected to correct the inclination of the head and the posture of the entire body. At this time, the patient's body is in a natural and relaxed state without inducing any difficulty in the patient's muscles and breathing. That is, in a case where the patient's head is inclined, a center-of-gravity line, which is obtained by using the weight 54 suspended from the strap member 51 through intermediation of the string-member, and the median line S of the patient should deviate from each other. Therefore, the inclination of the patient's head is modified such that the center-of-gravity line and the median line S match each other. In a case where the inclination of the head is modified as described above, at the plane member 52 is also inclined along with the inclination correction of the patient's head. Accordingly, the plane member 52 turns out not to level in the normal horizontal direction at the lower point of the ala nasi of the patient. Next, in a case where the center-of-gravity line and the median line of these head match with each other, the plane member 52 is adjusted again in such a direction that the level indicates horizontal at the lower point of the ala nasi of the patient. Through this operation, the corrected Camper's plane C can be obtained.

Figure 15:
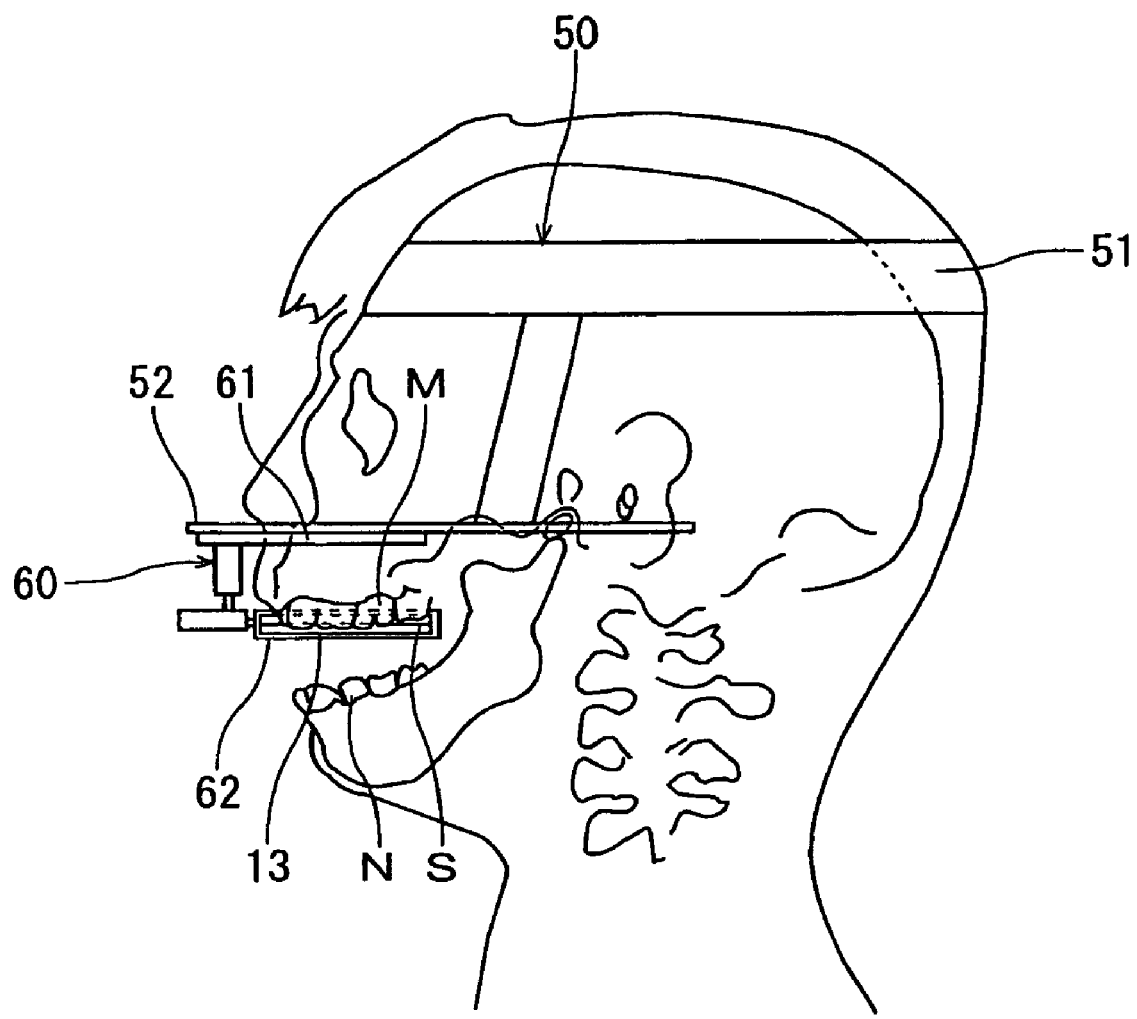
FIG. 15 is a schematic view illustrating a mounted state of a guide member.

The step of acquiring a plane C' in parallel to the corrected Camper's plane C will be described. In FIG. 15, a guide member 60 comprises a guide plate 61, and an insertion plate 62 parallel to the guide plate 61. The insertion plate 62 is provided as being able to be fixed at an appropriate interval while maintaining its parallel state relative to the guide plate 61. In the state having the plane-acquiring device 50 mounted on the head, the guide plate 61 of the guide member 60 is brought into intimate contact with the plane member 52 and, in this state, the insertion plate 62 is inserted onto the maxillary tooth row M within the oral cavity. The guide plate 61 is provided so that it may come into intimate contact with the plane member 52 as mounted so that its mounting position may be adjusted with adjustment screws (not shown), for example. In addition, a prescribed space S is left between the insertion plate 62 and the maxillary tooth row M. The insertion plate 62 becomes parallel to the Camper's plane C and the Camper's plane C is moved into the oral cavity to enable the plane C' to be acquired.

In the state mentioned above, a rubber material 13 that is a rubber-based or gypsum-based impression material is inserted under pressure into the space S between the insertion plate 62 and the maxillary tooth row M, and wax is poured into the space S to cure the rubber material 13. As a result, it is possible to obtain a tooth model-shaped surface of the maxillary tooth row M on one surface of the rubber material 13 and a plane parallel to the plane C' on the other surface thereof. The rubber material 13 is removed from between the insertion plate 62 and the maxillary tooth row M. Furthermore, the insertion plate 62 is provided so as to be detachable from the guide member 60, an arch member is attached along the maxillary tooth row M using a wire (not shown) etc. and the arch member is temporarily attached within the maxillary tooth row M in parallel to the plane C', thereby enabling the errors, such as positional displacement of the insertion plate 62, to be confirmed, thus ensuring accurate mounting of the insertion plate 62.

As described in the foregoing, in the step of acquiring the corrected Camper's plane, it is intended to obtain a corrected Camper's plane of the upper model 11 having formed the maxillary tooth row M. The headgear like plane-acquiring-device 50 is used, for example, to acquire a corrected Camper's plane C from the lower point of the ala nasi to the edge of the auditory meatus and subsequently the guide member 60 is used to form a plane C' in parallel to the acquired corrected Camper's plane C on the rubber material 13. In this way, the plane C' parallel to the corrected Camper's plane C can accurately be acquired without relying on dentists' own experiences and gut feelings.

In FIG. 2 to FIG. 5, an upper frame 15 and a lower frame 21 are molded from a resin material, such as a plastic resin etc. A molten resin material is poured onto the upper and lower models 11 and 12 to be able to closely contact the maxillary tooth row M and mandible tooth row N from the inside, thereby attaining a tooth model-shaped molding. Reference numerals 22 and 23 in FIG. 5 denote hook-shaped stopper members made of metal, for example, and which are provided at four places on the lower frame 21 for preventing the lower frame 21 from sinking toward the tongue. Of these stopper members, the deeper stopper members 22 are positioned within a so-called occlusal power zone within which a projection portion 41a is set in position. The occlusal power zone is called the origin of the oral function, is approximating clearness as an important occlusion function zone in practicing the constancy of the vital function of the entire body including the brain and is said to exist between the second bicuspid teeth $T_1$ and the first molar teeth $T_2$ of the maxillary tooth row M. The projection portion 41a of a first screw member 41 that will be described later is mounted as a positioning reference point between the second bicuspid teeth $T_3$ and the first molar teeth $T_4$ of the mandible tooth row N so as to correspond to the occlusal power zone. In this state, the lower frame 21 is mounted within the oral cavity, with the result that the lower frame 21 can be mounted at a most appropriate position relative to the center of gravity of the attracting force (tractional force). Thus, the upper frame 15 and lower frame 21 are positioned and fixed in a state in which the cross direction thereof has been adjusted relative to the maxillary and mandible tooth rows M and N.

Figure 11:
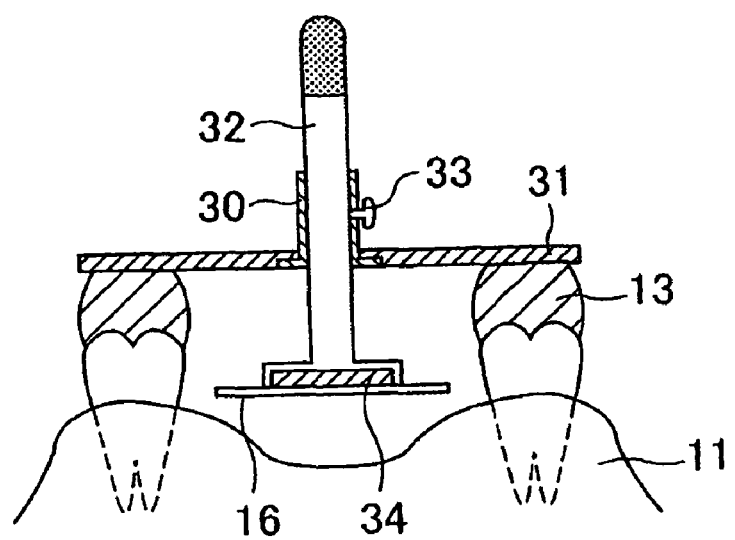
FIG. 11 is an explanatory view illustrating a mounted state of a mounting jig.
Figure 12:
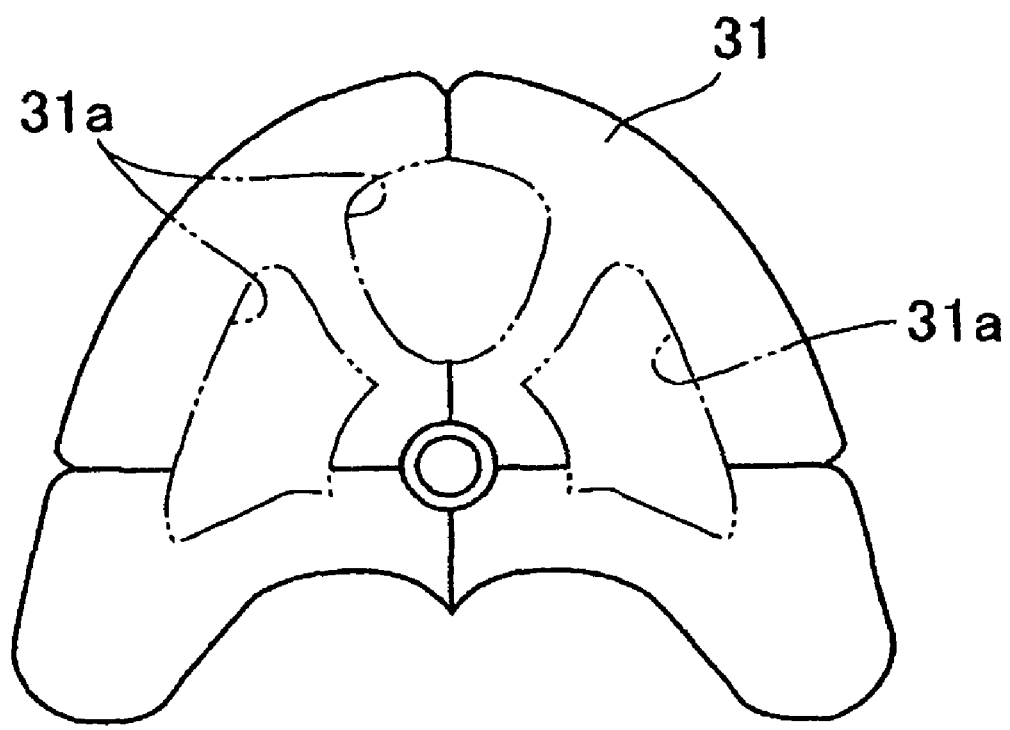
FIG. 12 is a plan view showing a flat plate.

The upper frame 15 is provided with a plate-shaped member 16 in parallel to the plane C' to thereby provide the upper frame 15 with the plane parallel to the Camper's plane C, taking the occlusal power zone into consideration. In FIG. 11, a mounting jig 30 is for mounting the plate-shaped member 16 on the upper frame 15. When mounting the plate-shaped member 16, the tooth model-shaped surface of the maxillary tooth row M for the rubber material 13 is placed on the upper model 11, and the mounting jig 30 is mounted while placing a flat plate 31 on the opposite surface of the rubber material 13 to thereby allow the inclination of the flat plate 31 to be identical with the plane C' of the rubber material 13. Thus, the plane having the same angle as the Camper's plane C can be obtained. Though the flat plate 31 is formed in a planar shape to make it easy to form the plane C', it may have through holes 31 as shown by the two-dot chain lines in FIG. 12.

The mounting jig 30 has a rod-shaped movable member 32 that can move vertically relative to the flat plate 31 and be fixed with a setscrew 33 in a state adjusted to an optional height. A magnetic flat plate 34 made of a magnet is attached to the distal end of the movable member 32 on the side of the upper model 11 in parallel to the flat plate 31. To the magnetic flat plate 34 the plate-shaped member 16 made of a material, such as stainless steel, to form a maxillary plate can magnetically attached. With this, the plane C' acquired on the rubber material 13 can be moved by means of the plate-shaped member 16 via the flat plate 31 and magnetic flat plate 34 while maintaining its parallel state, thereby enabling the plate-shaped member 16 to be mounted at an optional appropriate height.

In actually mounting the plate-shaped member 16 on the upper frame 15, the mounting jig is first mounted in the state in which the upper frame 15 has been mounted on the upper model 11, and the movable member 32 is vertically moved to cause the plate-shaped member 16 magnetically attached to the magnetic flat plate 34 to abut on a predetermined position of the upper frame 15. Subsequently, a resin material (not shown) that is the same material as the upper frame 15 and is in the form of liquid or powder is applied to the peripheral section of the plate-shaped member 16 with a brush. By removing the mounting jig 30 in the state in which the resin material has been solidified, the plate-shaped member 16 can be integrated with the upper frame 15 as pinched by the upper frame 15 and applied resin material to constitute an upper mold-mounting member 14 having the plate-shaped member 16 parallel to the Camper's plane C and mountable on the upper model in this step of forming the upper mold-mounting member. Incidentally, since the magnetic flat plate 34 is magnetically attached to the plate-shaped member 16, it can readily be detached from the plate-shaped member 16 after the plate-shaped member 16 is integrated with the upper frame 15.

Figure 2:
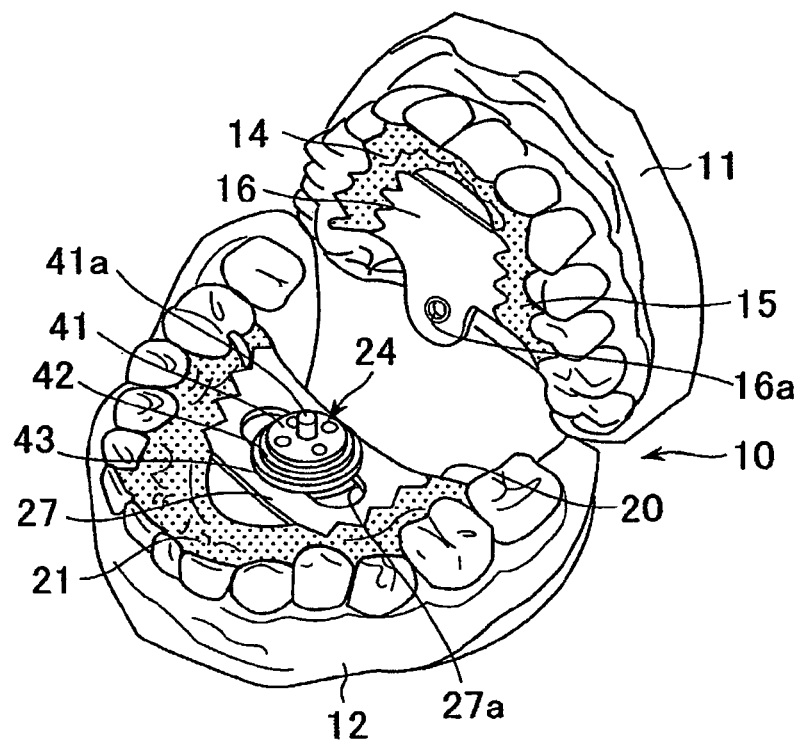
FIG. 2 is a perspective view showing the state of an occlusion correction improvement instrument according to the present invention mounted.
Figure 10:
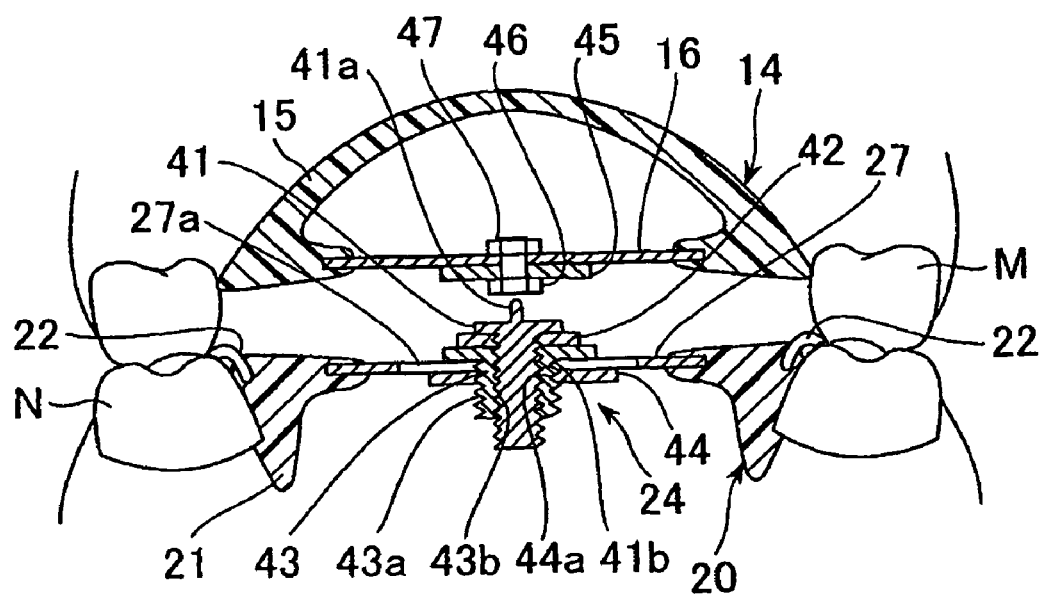
FIG. 10 is an enlarged cross section taken along line X-X in FIG. 3.

In FIG. 2 and FIG. 3, an adjustment member 24 of a lower mold-mounting member 20 comprises the first screw member 41, a second screw member 42, a third screw member 43, a fourth screw member 44 and a plate member 27. The third and fourth screw members 43 and 44 are helically engaged with each other via an oblong hole 27a bored in the plate member 27 at a male thread part 43a of the third screw member 43 and a female thread part 44a of the fourth screw member 44 (FIG. 10). The male and female thread parts 43a and 44a are moved from side to side in their loosened state to be fastened to each other, thereby mounting the male and female screw members 43 and 44 to be movable from side to side within a frame body 27a that is the oblong hole in the plate member 27. Also, the first screw member 41 is helically engaged with the third screw member 43 at a male thread 41b of the first screw member 41 and a female thread 43b of the third screw member 43, with the second screw member 42 intervening between the first and third screw members 41 and 43, thus mounting the first screw member 41 so as to vertically movable relative to the plate member 27. The height of the first screw member 41 is fixed with fastening by the second screw member 42, with the height of the first screw member 41 adjusted by the male and female threads 41b and 43b.

In this way, the pin-shaped projection portion 41a of the first screw member 41 in the adjustment member 24 is movable from side to side and up and down and can be fixed in a positioned state. Thus, the position of the projection portion 41a can smoothly and finely be adjusted without detaching the lower mold-mounting member 20 from the mandible, resulting in no possibility of affording repeated pains and uncomfortable feelings to the patient accompanied with the detachment of the lower mold-mounting member 20. Furthermore, the adjustment can be attained with ease when providing the first, second, third and fourth screw members 41, 42, 43 and 44 with through holes (not shown) and rotating them by means of a tool (not shown), such as a wrench, inserted into the through holes. Incidentally, the distal end of the projection portion 41a is formed into a semi-spherical shape in cross section.

Next, the lower frame 21 is mounted so that it may have an accurate positional relationship relative to the lower model 12 while confirming the position of the projection portion 41a to mount the adjustment member 24 on the lower frame 21, with the distal end of the projection portion 41a of the adjustment member 24 adjusted to be positioned at a lowest position from the lower frame 12. An adjustment is made so that the distal end of the projection portion 41a becomes in a state abutting on the plate-shaped member 16 when the lower model 14 having attached thereto the lower frame 21 on which the adjustment member 24 has been mounted and the upper model 11 having attached thereto the upper mold-mounting member 14 are subjected to occlusion. In the state, the adjustment member 24 is fixed to the lower frame 21. Thus, it is necessary to fix the adjustment member 24 to the lower frame 21 in the state in which the height of the adjustment member has accurately been adjusted.

When mounting the adjustment member 24, the same resin material as the lower frame 21 is applied to the adjustment member 24 from above with a brush etc. in the same manner as in the case of the upper-mold-mounting member 14. When the resin material has been solidified, the adjustment member 24 can be integrated with the lower frame 21 as being pinched by the lower frame 21 and the applied resin material to constitute the lower mold-mounting member 20 having mounted thereto the adjustment member 24 that has the projection portion 41a capable of abutting on the plate-like member 16. When the projection portion 41a has abutted on the plate-like member 16, the relative position between the upper mold-mounting member 14 and the lower mold-mounting member 20 becomes adjustable. In order to prevent induction of rattling and looseness between the upper and lower mold-mounting members when being mounted on the upper and lower models 11 and 12, respectively, it is desirable to polish the upper and lower mold-mounting members with an appropriate abrasive. Furthermore, it is necessary to confirm in advance whether or not the molded upper and lower models 11 and 12 match the tooth row state and occlusion state of the patient. If the models should have distortion and/or air bubbles, these have to be remodeled or remedied. Moreover, even after the upper and lower mold-mounting members 14 and 20 have been produced, it is necessary to confirm whether or not these can be mounted on the upper and lower models, respectively.

Figure 1:
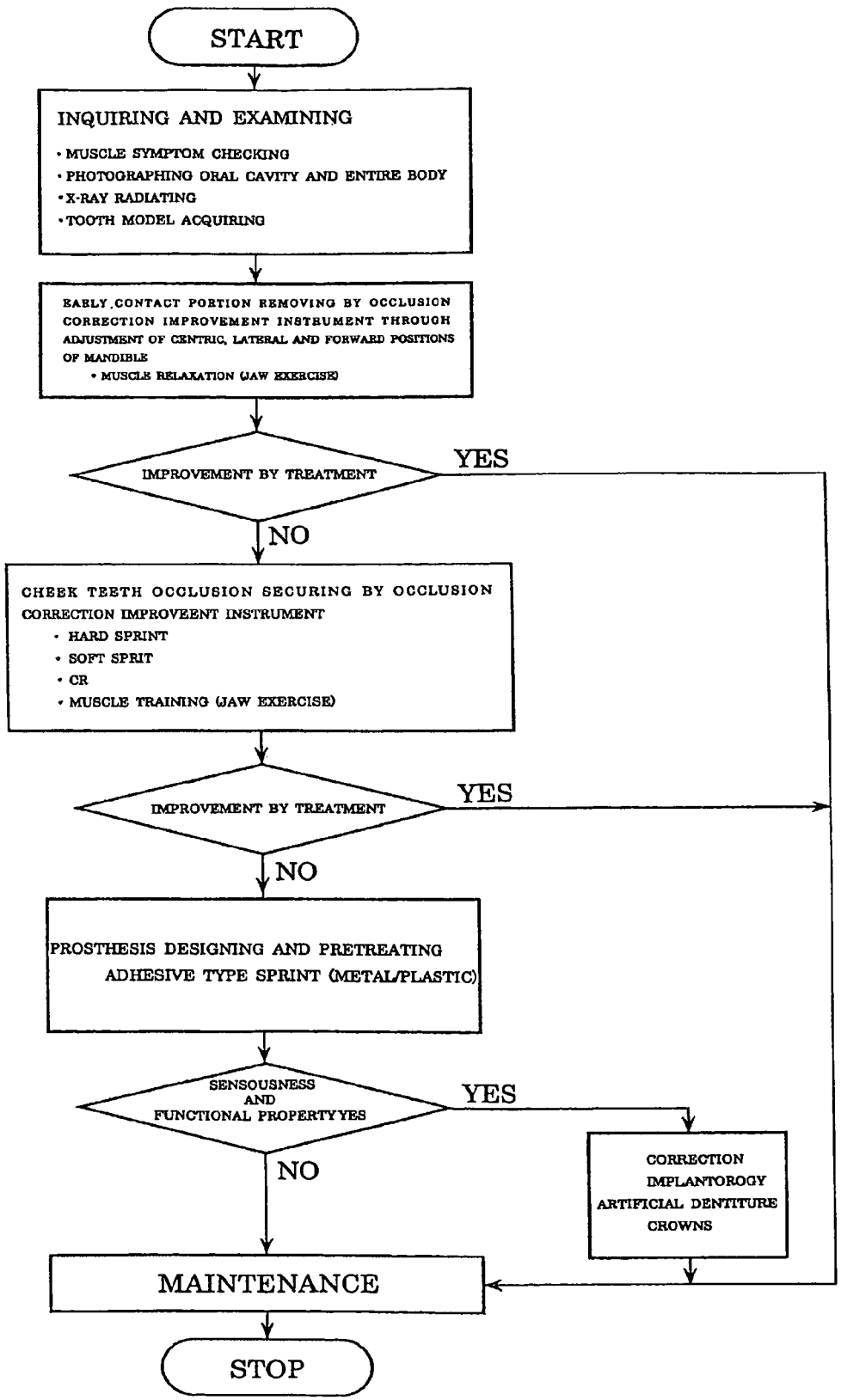
FIG. 1 is a flow chart illustrating the procedure of an occlusal treatment.

A correction improvement method using the occlusion correction improvement instrument and an operation of the occlusion correction improvement instrument of the embodiment mentioned above will be described. In the flowchart shown in FIG. 1, a dentist first asks a patient about his or her condition and examines the patient as described earlier. Based on the results thereof, the state of occlusion of the patient is diagnosed, the Camper's plane C is acquired on the maxillary tooth row M at the Camper's plane-acquiring step, and the plate-shaped member 16 is attached in parallel to the Camper's plane C to the upper frame 15 at the upper mold-mounting member formation step. Subsequently, the lower mold-mounting member 20 provided with the projection portion 41a that is capable of abutting on the plate-shaped member 16 is formed at the lower mold-mounting member formation step, and at the following correction step, the upper and lower mold-mounting members 14 and 20 are used to correct the maxillary and mandible tooth rows.

When mounting the upper and lower mold-mounting members 14 and 20 within the oral cavity, the projection portion 41a of the lower mold-mounting member 20 is allowed to abut on the center of the plate-shaped member 16 of the upper mold-mounting member 14 and, in this state, the first screw member 41 is rotated to widen the vertical interval between the mold-mounting members, thereby making adjustment to the effect that a gap is left between the maxillary and mandible tooth rows M and N when the upper and lower mold-mounting members have been mounted. Owing to the presence of this gap, the upper and lower teeth are brought to a state of non-contact even when the mandible has been moved back and forth and around. That is to say, this state is a state in which the position of occlusion of the mandible is lower than an ordinary position of occlusion. With this state maintained, the upper mold-mounting member 14 is removed from the maxillary tooth row M, and the surface of the plate-shaped member 16 is applied with a coating material so that the distal end of the projection portion 41a may describes its track on the coated surface of the plate-shaped member 16 when the projection portion 41a has abutted on the plate-shaped member. Thus, the projection portion 41a can function as a marking device.

At this time, the Camper's plane-acquiring step and upper mold-mounting member formation step are systemized to enable the plate-shaped member 16 to be mounted at the precise position as maintained in parallel to the Camper plane C. With this, the occlusion state of the maxilla and mandible can precisely be measured without inducing slippage of the distal end of the projection portion 41a on the plate-shaped member 16 when the maxilla and mandible has been subjected to occlusion or tapping motion, which slippage may possibly deviate the position of the mandible bone toward a position getting away from the stable position.

Figure 6:
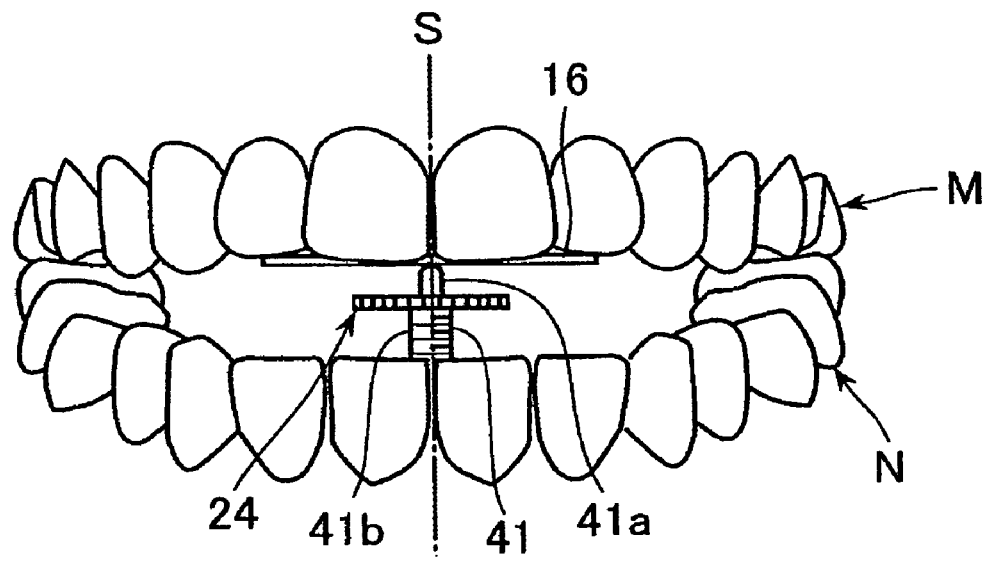
FIG. 6 is a front view showing the mounted state of the occlusion correction improvement instrument.
Figure 7:
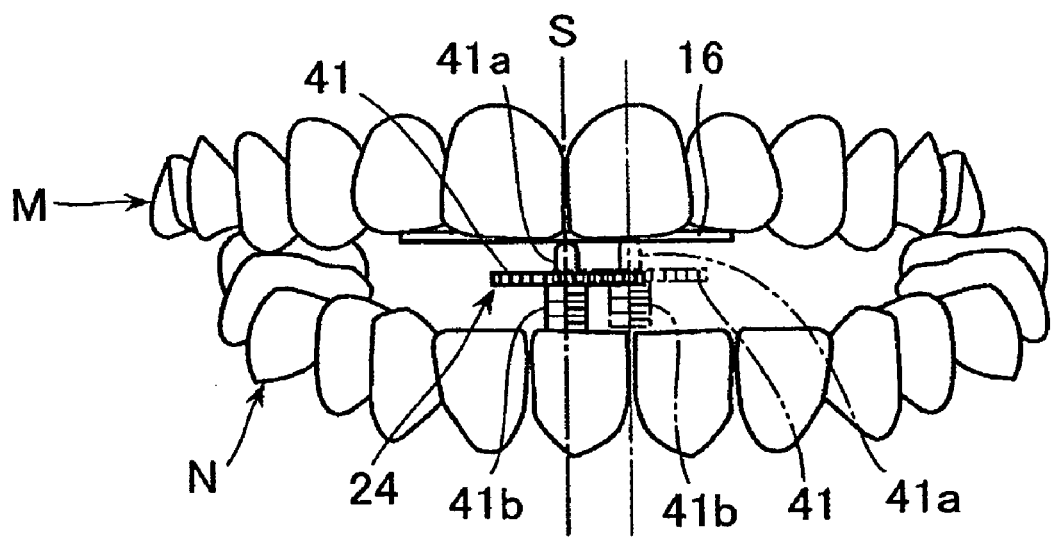
FIG. 7 is a front view showing an adjusted state of the occlusion correction improvement instrument.
Figure 8:
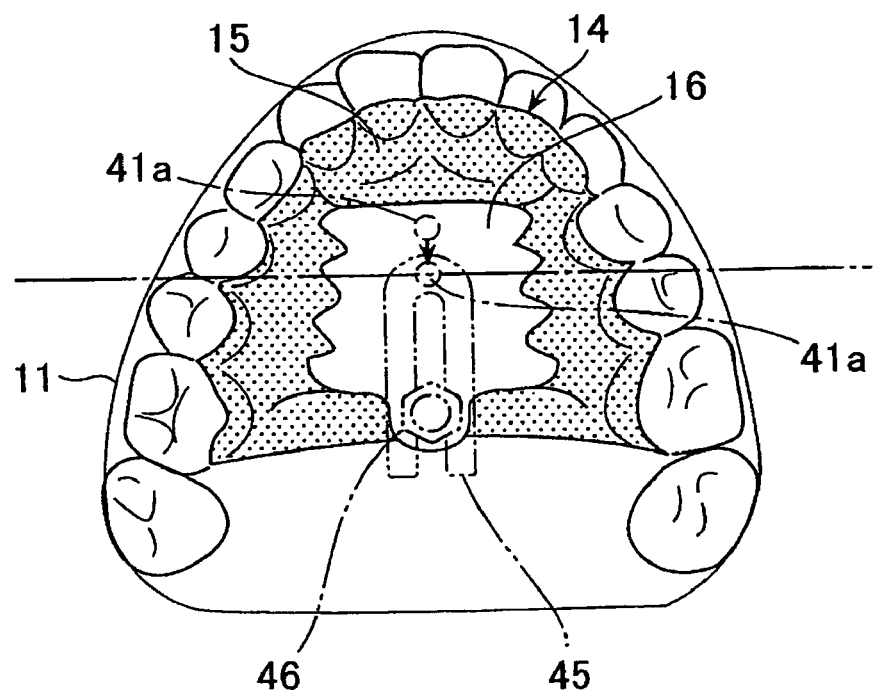
FIG. 8 is a plan view showing an adjusted state of the occlusion correction improvement instrument.

In case where the projection portion 41a fails to correctly abut on the neighborhood of the center of the plate-shaped member 16 as shown in FIG. 7 or FIG. 8 when the upper and lower mold-mounting members 14 and 20 have been mounted on the maxillary and mandible tooth rows M and N, respectively, the position of the projection portion 41a has to be adjusted. As a reason for the projection portion 41a abutting incorrectly on the plate-shaped member, right-and-left deviation of the maxilla of the patient relative to his or her mandible can be cited. In this case, the projection portion 41a is moved back and forth relative to the plate member 27 in the adjustment member 24 shown in FIG. 10, thereby enabling the projection portion 41a to be disposed infallibly in the vicinity of the center of the plate-like member 16. As a result, the projection portion 41a on the mandible can be positioned relative to the median line S of the maxilla, and the balance of the occlusion relative to the median line S can be achieved. Even in case where the mandible is shifted rightward or leftward relative to the median line S of the maxilla as shown in FIG. 7, unlike in FIG. 6 in which the mandible is correctly positioned relative to the median line S, the median line S of the mandible can be taken correctly relative to the maxilla. Also by the use of the stopper members 22 and 23 shown in FIG. 5, the maxilla and mandible can correctly be mounted without deviating the maxilla and mandible anteroposteriorly. Incidentally, the positional deviation of the maxilla and mandible can be improved through the correction treatment that will be described later.

Subsequently, the mandible of the patient is vertically moved to repeat tapping motion plural times, and dot-shaped traces described on the plate-shaped member 16 by the projection portion 41a are visually discerned. It is possible to confirm from the vertical tapping motion whether the mandible motion is constant during the mastication. When the dot-shaped traces described and left on the plate-shaped member 16 by the projection portion 41a through the tapping motion fall within a prescribed region, the patient is then subjected to marking motion by the back-and-force-and-around movement of the mandible, which motion will be described later. When the dot-shaped traces fall outside the prescribed region, this implies that the occlusion of the mandible relative to the maxilla is kept unequable, meaning an erratic occlusion state. Therefore, the treatment shown below will be given to the patient for the purpose of making the motion of the mandible during the occlusion constant.

In a case where the dot-shaped traces left through the tapping motion have fluctuations, the patient has dropped into a bad habit due to the mastication by undesirable prolonged occlusion of the maxillary and mandible tooth rows. The bad habit is caused by the deviation in working side and worked side during the mastication, chopping type occlusion, etc. Furthermore, the bad habit exerts stress on the muscles that move the maxillary and mandible tooth rows. Therefore, it is necessary to conduct a treatment for winding down the stress of the muscles. To wind down the stress of the muscles, a long and round cotton fiber called roll Watte is pinched between the maxillary and mandible tooth rows, for example. Otherwise, a mouthpiece-shaped soft or hard sprint is mounted on the tooth row to make up, during sleep, for example, a state in which the maxillary and mandible tooth rows are not in contact with each other, thereby depriving the muscles of stress. This treatment continues until the dot-shaped traces left through the tapping motion fall within the prescribed region.

Next, an early contact portion is confirmed from the track described on the plate-shaped member 16 during the movement of the mandible of the patient. By confirming the right-and-left early contact portion, in this case, the portion of contact made resulting from the working and worked sides can be confirmed. Though the mandible attempts to move so that the occlusion of the maxillary and mandible tooth rows may be naturally uniformly attained, uniform occlusion cannot yet be achieved due to the early contact portion. In this case, the muscle gets scent of the early contact portion and transmits it to the brain and, by the commands from the brain to perform the occlusion naturally avoiding the early contact portion, forced occlusion deviating from the natural desirable occlusion is performed. The mastication by the forced occlusion has been carried out over a long period to give rise to the patient. A non-contact state of the maxillary and mandible tooth rows is produced by the collision of the projection portion 41a on the plate-shaped member 16, and the non-contact space is gradually narrowed, thereby preventing the bad habit of the mandible motion resulting from the early contact portion of the tooth rows. In this state, contact features of the early contact portion can be three-dimensionally assessed.

When the dot-shaped traces through the vertical tapping motion has fallen within the prescribed region, the mandible is moved sidewise to describe a track on the plate-shaped member 16. A change in position on the plane C' of the lower mold-mounting member 20, parallel to the Camper's plane C, relative to the upper mold-mounting member 14 is visually discerned from the described track. In this case, when the track has been described linearly, the occlusion is kept stable. When the track has been described in a curved fashion, however, this shows an occlusion instable state. Next, while confirming the state of the track, the projection portion 41a is moved little by little downward, with the projection portion 41a adjusted with the first and second screw members 41 and 42, to gradually narrow the space between the maxillary and mandible tooth rows M and N and confirm the place of initial contact between the maxillary and mandible tooth rows M and N as the early contact portion.

After the confirmation of the early contact portion as described above, a grinding-in treatment for removing the early contact portion is performed, in which the center position (centric), lateral and forward positions of the mandible are adjusted to remove the early contact portion. The removal of the early contact portion can be attained through mounting of the occlusion correction improvement device within the oral cavity. This step and confirmation of the early contact portion are repeated to proceed with the treatment. When the occlusion symptom has been improved, the treatment is then completed, followed by maintenance of the maxillary and mandible tooth rows M and N.

In a case where the cheek teeth of the maxillary and mandible tooth rows are separate when having mounted the occlusion correction improvement instrument, it becomes necessary to secure the occlusion of the cheek teeth to start a next step of treatment. As a method of treatment, in this case, the height of the early contact portion is determined using a prescribed dental treatment instrument (not shown) to attain occlusion. Furthermore, a dental crown of resin is coated on a cheek tooth, a hard or soft sprint is mounted within the oral cavity for a prescribed time for the purpose of keeping the jaw joints and muscles in a quiet state to stabilize these, or a muscle training is executed, thereby perform the occlusion treatment. In this way, the occlusion of the cheek teeth is stabilized to make the occlusion uniform on the right and left sides at the time of occlusion of the maxillary and mandible tooth rows M and N.

In the case of this method of treatment, even when the treatment has improved the occlusion symptom, the confirmation of the occlusion state of the cheek teeth and the treatment are repeated two to three times. The reason for this is that even once the occlusion has been improved by the treatment, the jaw muscles that were elongated and contracted function in order to possibly produce again the deviation of the mandible. The repetition of the confirmation of the occlusion state and the treatment enables a complete cure of the deviation to be effected into finally correct occlusion. When the occlusion symptom has been improved here, the treatment is terminated, followed by maintenance of maxillary and mandible tooth rows M and N.

In a case where the occlusion cannot be secured even by the step of treatment mentioned above including excavation in a tooth, i.e. where the cheek teeth are separate due to small heights thereof, a next step of treatment is started. In the next step of treatment, the cheek teeth are subjected to prosthesis. In the prosthesis, a dental crown of metal or plastic, for example, is used to coat a cheek tooth to bury the gap and/or compensate for the height, thereby achieving occlusion of the cheek teeth in an optimum state. However, the prosthesis raises a problem in that the position of the lower mold-mounting member 20 mounted relative to the mandible tooth row N varies. This is because the positions of the four stopper members 22 and 23 of the lower mold-mounting member 20 engaged with the cheek teeth made higher become high.

Thus, even though the upper and lower mold-mounting members used so far should be mounted on the jaw tooth rows that have been subjected to the prosthesis, it would be impossible to visually discern the occlusion state with exactitude. This necessitates preparation of new upper and lower mold-mounting members. By mounting the newly prepared upper and lower mold-mounting members on the maxillary and mandible tooth rows after the prosthesis of the cheek teeth, a fresh occlusion state can visually discerned with exactitude, thereby enabling performance of the treatment after the prosthesis.

As described above, to infallibly attain accurate occlusion of the upper and lower cheek teeth, there are two cases, one excavating the cheek teeth and the other subjecting the cheek teeth to prosthesis. Thus, an appropriate treatment is to be made in accordance with the occlusion state of every one patient while visually discerning the state of occlusion of the maxillary and mandible tooth rows M and N using the occlusion correction improvement instrument. When the occlusion symptom has been improved here, the treatment is terminated, followed by maintenance of maxillary and mandible tooth rows M and N.

Moreover, as a next step of treatment, treatments such as tooth row correction, implantorogy and mounting of artificial dentitions and dental crowns with the aim at heightening the patient's sensousness, are made in accordance with patient's desires. In conducting these treatments, treatments appropriate to the patients are conducted while confirming the occlusion state when having mounted the upper and lower mold-mounting members. Even after the completion of the treatment of the maxillary and mandible tooth rows by means of the correction improvement method described above, it is desirable to conduct a maintenance treatment, such as a periodic medical examination utilizing the occlusion correction improvement instrument.

Here, the occlusion of the tooth rows and body balance will be described. Generally, when one's eyes are trained on the horizontal, the one's head is in an equilibrium situation. When the plane C' is parallel to the plane of occlusion of the upper and lower tooth rows (virtual occlusion plane) and the head portion of the mandible joint is in a correct state within the articular fossa, the balance between the center of gravity of the head and the gravitational line (median line) of a human body is best achieved. Though the center of gravity of the head varies depending on the position of the jaw joint, the occlusal treatment can bring the jaw position to a correct state, thereby enabling the center of gravity of the head to be in a correct state. Therefore, the indefinite complaint can be eliminated. At this time, the point of support of the head lies in the atlanto (first cervical vertebra), and the balance of the head and the human body is achieved by means of the head neck muscle.

It can be confirmed through visual discernment of the states of the weights 54 and 55 of the strap member 51 whether or not the center of gravity of the head could be corrected to a desirable state through the occlusal treatment, the horizontal deviation of the mandible relative to the brainpan can be confirmed, and the displacement of the head, such as the inclination of the head, can be measured. Completion of the occlusal treatment can be confirmed when the displacement of the head has been corrected and when the center of gravity of the head has correctly overlapped the median line. The state of head displacement includes forward-movement displacement in which the head moves forward in a large amount relative to the human body, extension displacement in which the head inclines upward, flexion displacement in which the head inclines downward, lateral fold displacement of the occipital bone and atlanto, rotary displacement of the atlanto and lower cervical vertebrae, a combination of the rotary displacement and the lateral fold displacement and lateral mobile displacement in which the head moves laterally. The normal or these abnormal states can accurately measured through the visual discernment of the weights 54 and 55.

The occlusion correction improvement instrument of the present invention can be formed in line with the shapes of the maxillary and mandible tooth rows and the mastication state by occlusion and mounted on the tooth rows of every one patient in an optimal state. When mounting the occlusion correction improvement instrument, occlusion is conducted in a non-contact state of the teeth of the maxillary tooth row M and those of the mandible tooth row N to make it possible to simply confirm the symptom of a patient and, in accordance with the patient's symptom, the occlusal treatment can be divided into an optimal number of steps, thereby making it possible to correct the occlusion of the patient with exactitude. Furthermore, since the plate-shaped member 16 is mounted substantially in parallel to the Camper's plane, appropriate occlusion of the maxilla and mandible is obtained, or the mandible bone can spontaneously be moved to a position at which the balance of the muscles and organs can be achieved relative to the maxillary bone during the tapping motion, thereby restoring to an essentially desirable jaw position. Therefore, any dentists having a similar technical level can acquire substantially the same treatment effect without relying on their own experiences and gut feelings to enable the indefinite complaint and entire body posture distortion to be eliminated.

As described in the foregoing, though the position of the mandible bone relative to the maxillary bone relates deeply to the indefinite complaint and entire body posture distortion, according to the occlusion correction improvement instrument, the occlusal treatment using as the reference the median line of the head that is the anatomical baseline is made to correct the occlusion and thereby cure even the human body distortion.

Also, since measures can be adopted while confirming the state of occlusion after the medical treatment with the occlusion correction improvement instrument every one step, a dentist can take an appropriate occlusal treatment without taking any unnecessary and excess treatment, whereas a patient can receive a short-period occlusion correction through the number of the treatment steps made smallest and hold down expenses.

Figure 4:
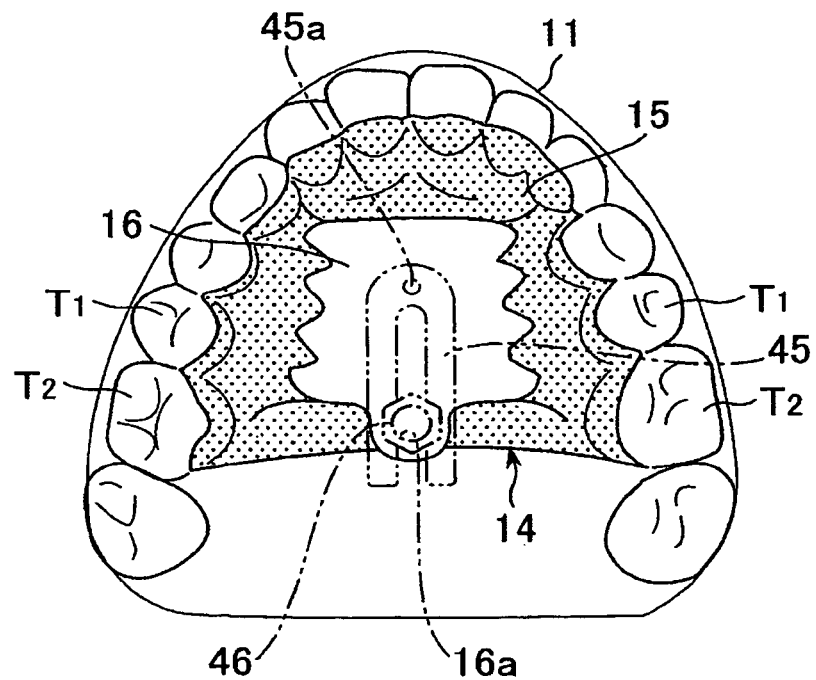
FIG. 4 is a plan view showing the state of an upper mold-mounting member mounted onto the maxilla.
Figure 5:
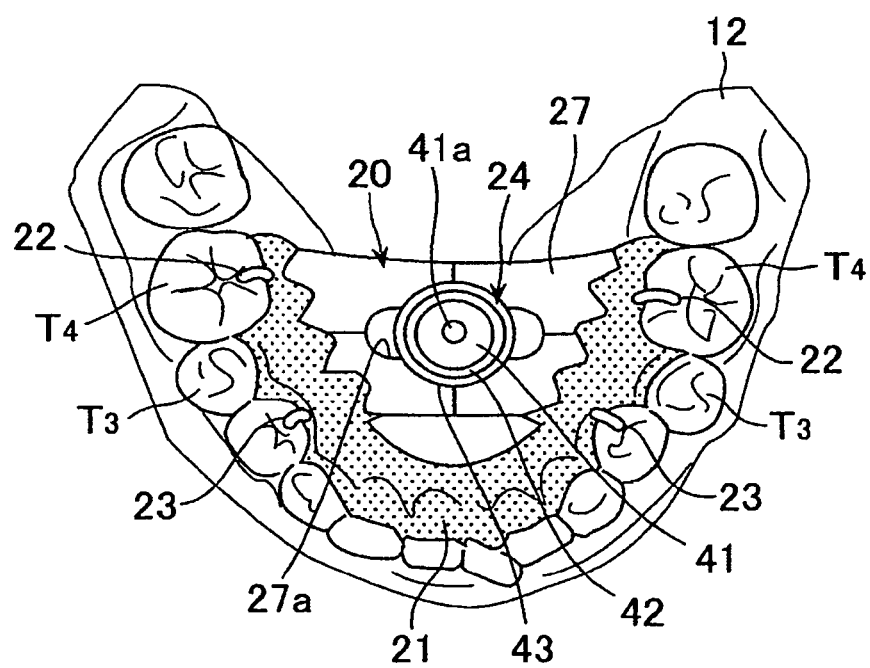
FIG. 5 is a plan view showing the state of a lower mold-mounting member mounted onto the mandible.

Incidentally, in the upper mold-mounting member 14 as shown in FIG. 4 and FIG. 10, a substantially U-shaped temporary fixation member 45 is temporarily fixed to a bolt hole 16a in the plate-shaped plate 16 with a bolt 46 and a nut 47. By changing the position of the temporary fixation of the temporary fixation member 45, the position of an insertion hole 45a in the temporary fixation member 45 can be changed. When the adjustment member 24 and temporary fixation member 45 are temporarily fixed, with the projection portion 41a inserted into the insertion hole 45a, the temporarily fixed state can be maintained, and the positional relationship of the upper and lower mold-mounting members 14 and 20 can be retained. Therefore, by mounting the upper and lower mold-mounting members 14 and 20 on the maxillary and mandible tooth rows M and N, respectively, subjecting the maxillary and mandible tooth rows M and N to occlusion to insert the projection portion 41a into the insertion hole 45a and confirming a click from the insertion, it is possible to confirm that the lower mold-mounting member 20 (mandible) is in an appropriate position relative to the upper mold-mounting member 14 (maxilla) and that the occlusion of the maxillary and mandible tooth rows M and N is appropriate. Thus, use of the temporary fixation member 45 after the tooth row correction enables the correction results to be confirmed with ease.

The invention claimed is:

1. An occlusion correction improvement instrument comprising: a lower mold-mounting member that, in order to balance an occlusion of a maxilla and a mandible of a patient, is arranged so as to correct a Camper's plane value of a head of the patient based on an inclination of a center-of-gravity line in a state where the patient is upright with respect to a direction of gravity, the lower mold-mounting member being arranged such that a relative position of the lower mold-mounting member on a plane parallel to a corrected Camper's plane is adjustable; and
a corrected Camper's plane-acquiring device, wherein the corrected Camper's plane-acquiring device includes
a strap member to be mounted on the head,
a plane member suspended from the strap member, the plane member being arranged to be laid in a direction extending across a face of the patient, the plane member having a boomerang shape,
a plane-measuring member provided substantially at a center of the plane member, and
a weight suspended from a distal end of a string member attached to a center of a face side of the strap member.

2. The occlusion correction improvement instrument according to claim 1, wherein the plane-measuring member comprises a level, and wherein a vicinity of the plane member is provided with markings at constant intervals so as to enable visual measurement of a deviation amount of the string member from the center-of-gravity line.

3. An occlusion correction improvement instrument comprising:
an upper mold-mounting member provided with a plate-shaped member mounted so as to be parallel to a corrected Camper's plane obtained by correcting a Camper's plane of an upper model having a tooth model-shaped surface of a maxillary tooth row based on a gravitational pull and an inclination of a center of gravity of a patient's head, the upper mold-mounting member being arranged to be mounted on the upper model and at a plane parallel to the corrected Camper's plane;
a lower mold-mounting member mountable on a lower model having a tooth model-shaped surface of a mandible tooth row, the lower mold-mounting member having a pin-shaped projection portion mounted such that a position of the pin-shaped projection portion can be fixed, with the position thereof being adjustable in a lateral direction and in a vertical direction, the lower mold-mounting member also having an adjustment member for adjusting a position of the lower mold-mounting member relative to the upper mold-mounting member on the plane parallel to the corrected Camper's plane, with the projection portion being arranged to abut on the plate-shaped member of the upper mold-mounting member; and
a corrected Camper's plane-acquiring device, wherein the corrected Camper's plane-acquiring device includes
a strap member to be mounted on the head,
a plane member suspended from the strap member, the plane member being arranged to be laid in a direction extending across a face of the patient, the plane member having a boomerang shape,
a plane-measuring member provided substantially at a center of the plane member, and
a weight suspended from a distal end of a string member attached to a center of a face side of the strap member.

4. An occlusion correction improvement method comprising:
correcting a Camper's plane of an upper model based on a gravitational pull and an inclination of a center of gravity of a patient so as to obtain a corrected Camper's plane, the upper model having a tooth model-shaped surface of a maxillary tooth row;
acquiring a plane parallel to the corrected Camper's plane;
forming an upper mold-mounting member that comprises an upper frame mountable on the upper model and a plate-shaped member attached to the upper frame so as to be parallel to the parallel plane;
forming a lower mold-mounting member that comprises a lower frame mountable on a lower model having a tooth model-shaped surface of a mandible tooth row, and that also comprises an adjustment member attached to the lower model and provided with a pin-shaped projection portion that is movable in a lateral direction and in a vertical direction relative to the lower frame and that is capable of abutting on the plate-shaped member of the upper mold-mounting member; and
correcting an occlusion, wherein the correcting of the occlusion includes at least one of adjustment of a position of the projection portion, adjustment of a position of the lower mold-mounting member relative to the upper mold-mounting member in the presence of a change of the relative position from a state in which the projection portion abuts on the plate-shaped member in a vicinity of a center portion thereof, and a pretreatment of excavation or prosthesis.

5. The occlusion correction improvement method according to claim 4, wherein said correcting of the Camper's plane comprises:
arranging a plane member, which is formed in a shape of a boomerang and has a level at a center thereof, so as to extend in a direction crossing a face of the patient and such that the level indicates horizontal at a lower point of an ala nasi of the patient, the plane member being suspended from a strap member to be mounted on a head of the patient;
inclining the head of the patient such that, on a center of a face side of the strap member, a center-of-gravity line obtained by a weight suspended from the strap member through intermediation of a string member and a median line of the patient match each other; and
readjusting, in a state in which the center-of-gravity line and the median line of the patient match each other, the plane member so that the level again indicates horizontal at the lower point of the ala nasi of the patient.

6. The occlusion correction improvement method according to claim 5, further comprising:
correcting a deviation amount of the string member on which the weight is suspended from the center-of-gravity line by using markings as a reference, the markings being provided substantially in a vicinity of the center of the plane member at constant intervals.

7. The occlusion correction improvement method according to claim 6, wherein the forming of the upper mold-mounting member includes mounting the plate-shaped member on the upper mold-mounting member using a jig for acquiring the plane parallel to the corrected Camper's plane of the upper model.

8. The occlusion correction improvement method according to claim 7, wherein the lower mold-mounting member is further formed to include a plate member having a frame body, and such that the projection portion has a proximal part helically engaged with the plate member so as to be movable in the vertical direction relative to the plate member and so as to be movable in the lateral direction relative to the frame body.

9. The occlusion correction improvement method according to claim 6, wherein the lower mold-mounting member is further formed to include a plate member having a frame body, and such that the projection portion has a proximal part helically engaged with the plate member so as to be movable in the vertical direction relative to the plate member and so as to be movable in the lateral direction relative to the frame body.

10. A corrected Camper's plane-acquiring device for obtaining a Camper's plane value of a head of a patient based on an inclination of a center-of-gravity line in a state where the patient is upright with respect to a direction of gravity, comprising:

a strap member to be mounted on the head;
a plane member suspended from the strap member, the plane member being arranged to be laid in a direction extending across a face of the patient, the plane member having a boomerang shape;
a plane-measuring member provided substantially at a center of the plane member, and
a weight suspended from a distal end of a string member attached to a center of a face side of the strap member.

* * * * *